United States Patent [19]

Abdullah

[11] Patent Number: 5,932,472
[45] Date of Patent: Aug. 3, 1999

[54] METHOD FOR DEGRADATION OF POLYCHLORINATED BIPHENYLS IN SOIL

[75] Inventor: Shahid Abdullah, Ancaster, Canada

[73] Assignee: Twin Oaks Envirormental Ltd., Ontario, Canada

[21] Appl. No.: 08/812,755

[22] Filed: Mar. 6, 1997

[30] Foreign Application Priority Data

Mar. 6, 1996 [GB] United Kingdom .................... 9604783

[51] Int. Cl.⁶ ...................................... C12S 13/00
[52] U.S. Cl. .................... 435/262.5; 435/262; 435/252.4
[58] Field of Search .................................. 435/42, 252.4, 435/262, 262.5

[56] References Cited

U.S. PATENT DOCUMENTS

| | | | |
|---|---|---|---|
| 4,391,887 | 7/1983 | Baumgarten et al. | 435/42 |
| 4,493,895 | 1/1985 | Colaruotolo et al. | 435/262 |
| 4,843,007 | 6/1989 | Bedard et al. | 435/262 |
| 4,843,009 | 6/1989 | Bopp | 435/262 |
| 5,324,661 | 6/1994 | Hazen | 435/262.5 |
| 5,340,376 | 8/1994 | Cunningham | 71/6 |
| 5,401,413 | 3/1995 | Gatt et al. | 210/610 |
| 5,635,393 | 6/1997 | Bhatnagar et al. | 435/262.5 |

FOREIGN PATENT DOCUMENTS

| | | | |
|---|---|---|---|
| 36 01 979 | 7/1987 | Germany | 435/262.5 |
| 92/13953 | 8/1992 | WIPO . | |

OTHER PUBLICATIONS

Davison et al. "Storage of a mixed microbial consortium capable of growth on biphenyl." Letters in Applied Microbiology. vol. 17 (1993), pp. 101–103.

STN: EMBASE Abstract AN:94196203 of Davison et al. "Synergistic growth of two members from a mixed microbial consortium growing of biphenyl." FEMS Microbiology Ecol. vol. 14 (1994), pp. 133–146.

Pettigrew et al. "Chlorinated Biphenyl Mineralization by Individual Populations and Consortia of Freshwater Bacteria." Applied and Environmental Microbiology. vol. 56, No. 7 (Jul. 1990), pp. 2036–2045.

R. Clark et al.; Degradation of Polychlorinated Biphenyls by Mixed Microbial, *Applied and Environmental Microbiology* 37, No. 4:680–685 (1979).

*Primary Examiner*—William H. Beisner
*Attorney, Agent, or Firm*—Alston & Bird LLP

[57] ABSTRACT

The present invention is directed to a method for the safe and efficient degradation of Polychlorinated biphenyls (PCBs) in PCB contaminated soil into non-hazardous by products. The method comprises adding a culture containing at least six strains of microorganisms capable of degrading PCBs to PCB contaminated soil, mixing the soil and microorganism culture together and maintaining the culture under stringent conditions which promote the growth of the microorganisms and which stimulate the ability of the microorganisms to degrade the PCBs. The method is cost efficient and well suited for decontaminating soil on a large scale commercial basis.

17 Claims, 5 Drawing Sheets

METHOD FOR DEGRADATION OF POLYCHLORINATED BIPHENYLS IN SOIL

FIELD OF THE INVENTION

The present invention relates in general to a method for the decontamination of soil and more particularly to a method for the degradation of polychlorinated biphenyls (PCBs) in soil.

BACKGROUND OF THE INVENTION

Polychlorinated biphenyls (PCBs) belong to a family of organic chemicals known as chlorinated hydrocarbons. They are commercially produced by the direct chlorination of biphenyl. Up to ten chlorine atoms may be attached at various locations on the biphenyl molecule which results in a possible 209 PCB compounds. PCBs are very stable and exhibit low water solubility, low vapour pressure, low flammability, high heat capacity and low electrical conductivity, making them extremely useful for a number of industrial purposes, including acting as an insulator in electrical capacitors and transformers. However, there are a number of adverse environmental and health effects associated with the use of PCBs. Earlier studies have shown that PCBs are the precursor molecules for a variety of environmentally hazardous compounds such as dioxin and furan. PCBs are known to cause malignant transformation of cells in humans. Such cellular toxic effects have also been demonstrated in experiments where laboratory animals have been repeatedly exposed to low levels of PCBs. The toxic effects of PCBs on both humans and animals together with the fact that PCBs excessively persist in the environment both point to the fact that PCBs have the potential to seriously affect man and the earth's ecosystems.

PCBs enter the environment in a number of ways. First, it has been estimated that more than half of the PCBs produced have been discarded in landfill sites and dumps. Contaminants washed out from such sites can enter ground water or are carried by rain and snow into nearby streams and rivers, finding their way into lakes and oceans. Second, incomplete combustion of PCB-containing wastes may release contaminants into the atmosphere in combustion gases that return to earth in rain or snow or as dry minute particles. Third, leaks from electrical transformers and capacitors seep into the soil, working their way into the environment. Fourth, liquids containing PCBs have been sprayed on roads in the past to act as a dust suppressant. Runoff from these roads drain into urban and rural sewage and drainage systems and into the environment. Finally, illegal dumping or disposal of PCBs by careless individuals or corporations results in contamination of the environment with PCBs.

The destruction of PCBs in the environment is the ultimate goal in PCB waste management, environmental cleanup and soil reclamation. Numerous technologies directed at effectively breaking down the molecular structure of PCBs into non-hazardous products have been developed. Two of these technologies, high-temperature incineration and chemical dechlorination, are currently being used on a commercial basis in a number of countries around the world. High temperature incineration, however, suffers from the drawback that it requires sophisticated and expensive equipment to perform the incineration. Chemical dechlorination requires the use of expensive chemicals and suffers from additional problems of disposal and environmental pollution from the resultant products from the chemical dechlorination.

A third technology, bioremediation, is an approach that can avoid further environmental problems and has advantages over incineration and chemical dechlorination in adaptability and cost. Bioremediation refers to the conversion of toxic environment contaminating compounds into innocuous substances by way of microbial digestion. Biodegradation of PCBs usually leads to the dechlorination of PCBs and formation of biphenyls and their derivatives. There has been much study on the use of bacteria for biodegradation of chlorinated biphenyls. It has been reported that certain strains of *Alcalignes eutrophus* and Pseudomonas sp. are effective for biodegradation of PCBs in river and lake sediments (Clark et al., 1979, Applied and Environmental Microbiology, Vol.37. No.4). However, several of these methods employed in these studies are not directed to a cost effective process which can be used on a large scale for the effective degradation of PCBs in soil.

U.S. Pat. No. 5,340,376 discloses a biological remediation process wherein microorganisms are employed to degrade contaminating organic compounds present within an environment. The process comprises applying a low-level of controlled-release source of microorganism nutrients capable of continuously supplying an effective microorganism growth and activity promoting level of nutrients over a period of at least two months. The controlled release nutrients are in the form of coated solid particles.

U.S. Pat. No. 4,391,887 discloses a process for the production of a storage-stable preparation of microorganisms capable of degrading products of industrial organic synthesis. The stabilised active mixed culture of microorganisms are treated with chemicals and then dried to obtain a storage-stable active mixed culture.

U.S. Pat. No. 5,401,413 discloses a composition for enhancing the biodegradation of biodegradable organic wastes which comprises the use of liposomes to supply essential nutrients for bacterial growth of microorganisms and at the same time, increase the polarity, wettability and availability of organic waste for enhancing bacterial interaction with the waste.

U.S. Pat. No. 4,493,895 discloses a method for the microbial degradation of halogenated organic chemical waste. The process comprises applying specifically designed strains of microorganisms capable of degrading the halogenated organic chemicals to carbon dioxide, water and salt. The microorganism strains have been engineered to contain a plasmid which confers the ability of decomposing halogenated organic chemicals.

While it is apparent that several bioremediation process exist for degrading toxic compounds in wastes, none of the processes are well adapted for large scale commercial use. Furthermore, none of the processes can achieve an optimal and desirable level for the degradation of PCBs in soil.

It is therefore an object of the present invention to provide an improved and efficient method for the microbial degradation of polychlorinated biphenyls in soil compared with other known waste decontamination procedures currently practiced today.

SUMMARY OF THE INVENTION

In accordance with the present invention there is provided a novel and improved method for the microbial degradation of polychlorinated biphenyls in soil into non-hazardous by products. The present method overcomes the disadvantages associated with traditional types of soil decontamination methods typically conducted as described previously. The method is easy to use and cost effective such that it is adaptable to be used on a wide commercial scale. The method of the present invention decreases the amount of PCBs in the soil so that the soil may be used for residential, industrial or commercial purposes.

In accordance with an object of the present invention there is provided a method for the microbial degradation of polychlorinated biphenyls in soil into non-hazardous by products, said method comprising;

(a) adding a culture containing at least six strains of microorganisms capable of degrading polychlorinated biphenyls to polychlorinated biphenyl contaminated soil; and (b) mixing the soil and microorganism culture and maintaining the mixture under stringent conditions which promote the growth of the microorganisms and which stimulate the ability of the microorganisms to degrade the polychlorinated biphenyls.

The inventive method is based upon the discovery that efficient degradation of PCBs in soil can be achieved when a combination of at least six species of bacteria are applied to PCB contaminated soil and maintained under a specific set of environmental conditions including temperature, moisture content, pH, oxygen levels and nutrient levels which promotes the growth of the microorganisms and their ability to degrade PCBs.

In accordance with another object of the present invention is a culture of microorgansims comprising at least Pseudomonas sp., Acinetobacter sp., *Alcaligenes eutrophus*, Polygonum sp., Digitaria sp., Bacillus sp. and Micrococcus sp. This culture is added and mixed with the contaminated soil under specific conditions which promote the growth and PCB degrading ability of the microorganisms.

In accordance with another object of the present invention is the addition of a surfactant to the contaminated soil to be treated. The surfactant enhances the degradation of PCBs in the soil. Preferably the surfactant is alkylenebenzene sulfonate.

BRIEF DESCRIPTION OF THE DRAWINGS

Embodiments of the present invention will now be described more fully with reference to the following drawings in which.

DETAILED DESCRIPTION OF THE PREFERRED EMBODIMENTS

Although there has been expended a great deal of effort into providing a bioremediation method which could be practically applied in order to clean land fill sites, no such effective method is currently in use or exists. We have now found that PCB contaminated soil can be decontaminated using a culture of at least six microorganisms capable of degrading PCBs. The microorganism is added and mixed with the contaminated soil and the mixture is then maintained under strict conditions which promote the growth of the microorganisms as well as their ability to degrade the PCBs. The mixture of the PCB contaminated soil and the microorganism mixture must be maintained at an appropriate pH, temperature, moisture, oxygen content and nutrient content in order for the method to effectively reduce PCB contaminated soils.

The PCB degradation method of the present invention required the isolation and culture of PCB tolerant microorganisms, as well as optimising the assay conditions required for optimal PCB degradation. It was also required that the following determination be made: optimal bacterial culture conditions for commercial application; proper removal and preparation for treatment of contaminated soil; and a treatment of contaminated soil. Once the soil has been treated and remediated, it can be returned to the original site, and the site may be used for industrial, commercial or residential purposes.

It is to be understood that any PCB contaminated soil can be decontaminated using the method of the present invention. Such soil can be typically found in land fill sites, near industrial chemical plants and elsewhere where PCBs were and can be released to the environment.

Isolation and Culture of Microorganisms from PCB Contaminated Soil

It was necessary at the outset to isolate bacteria which could survive in and metabolize PCBs contained in soil. Without being confined to any particular theory, it is believed that certain microorganisms have probably adapted to survive in PCB contaminated soil. It was therefore necessary to isolate and identify such microorganisms which could be further manipulated by altering their environmental condition in order to provide a culture of microorganisms capable of degrading PCB contaminated soil in a rapid and efficient manner.

For this purpose, soil contaminated with PCBs was obtained from a land fill site. It is understood that any land fill site containing these microorganisms is appropriate. About 50 g of the soil and 150 ml of phosphate buffer were mixed on a rotory shaker for about 5 minutes. The soil was centrifuged for 5 minutes and supernatant was decanted into a sterile flask. The supernatant (0.1 ml) was plated on commercially available MYP agar plates using a serial dilution up to $10^{-6}$ and incubated for overnight at 32° C. Several single colonies were further streaked onto 50 MYP agar plates and left in an incubator (32° C.) again overnight. There were about one hundred different colonies identified from the incubation. It was found that many of the species incubated were native to the soil and were not involved in the degradation of PCBs in the soil. Of the remaining species of bacteria that were involved in the degradation of PCBs, it was found that different species of bacteria degraded PCBs in soil at different rates. This is due to the fact that different bacteria have different rates of metabolism, and that some bacteria expend their energies degrading not only PCBs in the soil, but also other hydrocarbons present in the soil.

Further culturing of the bacteria using standard microbiological techniques identified the following six species of bacteria: Pseudomonas sp., Acinetobacter sp., Alcaligenes eutrophus, Polygonum sp., Digitaria sp., Bacillus sp. and Micrococcus sp.

The cultures of microorganisms are frozen for extended storage. When needed, the cultures are thawed and re-innoculated on agar plates where they are left to grow in an incubator until required for use in the present method.

The method of the present invention is characterized by applying the above bacterial species to PCB contaminated soil under the bacterial growth conditions described below. It is to be understood by those skilled in the art that the invention is not restricted to only these six microorganisms Other microorganisms, isolated from PCB contaminated soil, may also be useful in the method of the present invention.

Determination of Optimal Culture Conditions for Commercial Application

Any functional activity of microorganisms in soil is primarily reflected by their viability and active growth in the soil. There are a number of factors which are essential for the viability of microorganisms in soil, such as: temperature, moisture, pH, oxygen and nutrient level. A multitude of experiments were performed in which each of these factors were independently studied.

For each of the experiments, clean soil from agricultural land was obtained and tested to ensure there was no contamination by PCBs or foreign bacteria. The conditions of: temperature, moisture, pH, oxygen, nutrient level, surfactant and concentration of microorganisms, for the experiments was each individually adjusted as described below.

The temperature was controlled by and measured using standard laboratory thermometer equipment. A nutrient and water mixture of 1% calcium chloride, 1% ferric chloride, 1% ammonium chloride, 1% magnesium sulphate, 1% phosphate buffer and 95% water was prepared (all percentages based on weight). Moisture, pH, oxygen and nutrient levels were determined by taking samples every 48 hours, measuring the moisture level and the levels of oxygen, nitrogen, phosphorus, iron, magnesium and pH using commercially available laboratory equipment. The levels were adjusted and controlled by adding either water or the amount of nutrient and water mixture as necessary to maintain the soil within the test parameters. The level of pH was controlled by the addition of phosphate buffer. The level of oxygen was controlled by constantly purging the soil with air to maintain levels within test parameters. Alkylenebenzene sulphonate was added as a surfactant to counteract partitioning of microorganisms from PCBs in the soil.

PCBs were added to the soil by spraying, mixing and measuring levels until the level of PCBs was brought to 108 parts per million for the commencement of the tests. The level of PCBs was measured using gas chromotograph and electron capture detection equipment. A culture of the above mentioned six microorganisms was prepared from the inoculation of the microorganisms into a commercially available lactose (LB) broth and leaving it on a rotory shaker for about 4–5 hours at 32° C. Aliquots of culture were mixed with the soil containing PCBs for the assay and measured for its ability to degrade PCBs in the soil. The number of bacteria in the soil was measured by taking samples initially and every 48 hours thereafter using the standard serial dilution method to determine the number of Colony Forming Units (CFU) in the sample. Additional aliquots were added as necessary to maintain levels within test parameters.

As mentioned above, multiple experiments were conducted of different permutations of levels of each of the following components: concentration of microorganisms, temperature, moisture, pH, oxygen, nutrient level and surfactant. A summary of the results of the experiments are illustrated in FIGS. 1 to 8 which show the effect varying one of each of the parameters, when all of the other parameters was maintained at optimal. The optimal levels of each of the parameters was determined as follows:

concentration of microorganisms: $25 \times 10^8$–$35 \times 10^8$ CFU temperature: 32 degrees Celsius moisture: 25–35% pH: 6–8 oxygen: 1.5–2.0 equimolar nutrient level: 5–10% surfactant: 1%

Figure 1:
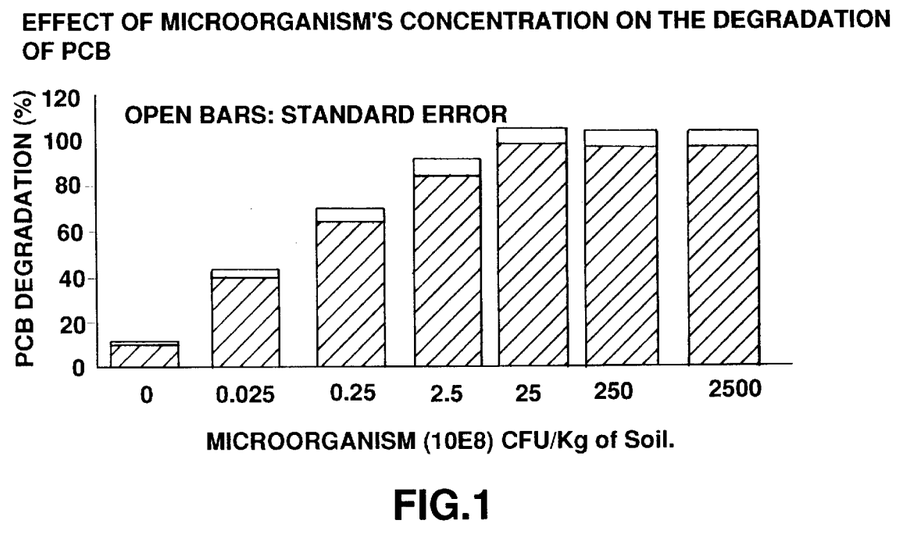
FIG. 1 shows the effect of microorganism concentration on the rate of degradation of PCBs in accordance with the present invention.

As shown in FIG. 1, the degradation of PCBs is proportional to the concentration of microorganisms in soil. It was determined that the concentration of microorganisms required to degrade PCBs in soil was $25 \times 10^8$ CFU/kg soil–$35 \times 10^8$ CFU/kg soil. Preferred ranges were from $25 \times 10^8$–$25 \times 10^{10}$ Colony Forming Units (CFU) per kilogram of soil.

Figure 2:
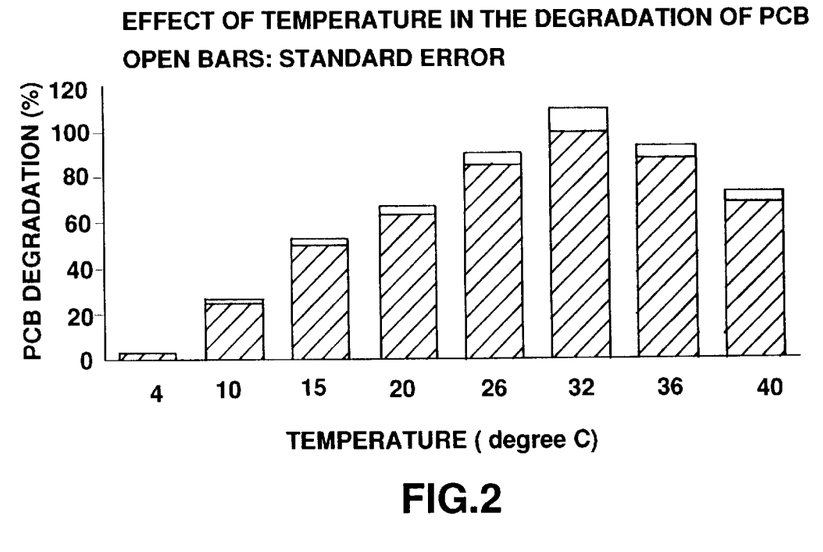
FIG. 2 shows the effect of temperature on the degradation of PCBs in accordance with the present invention.

As is apparent from FIG. 2, the degradation of PCBs in the soil was most efficient when the temperature was maintained around 32° C. whereas PCB degradation was significantly decreased at extreme temperatures which demonstrates that the microorganisms were temperature sensitive.

Figure 3:
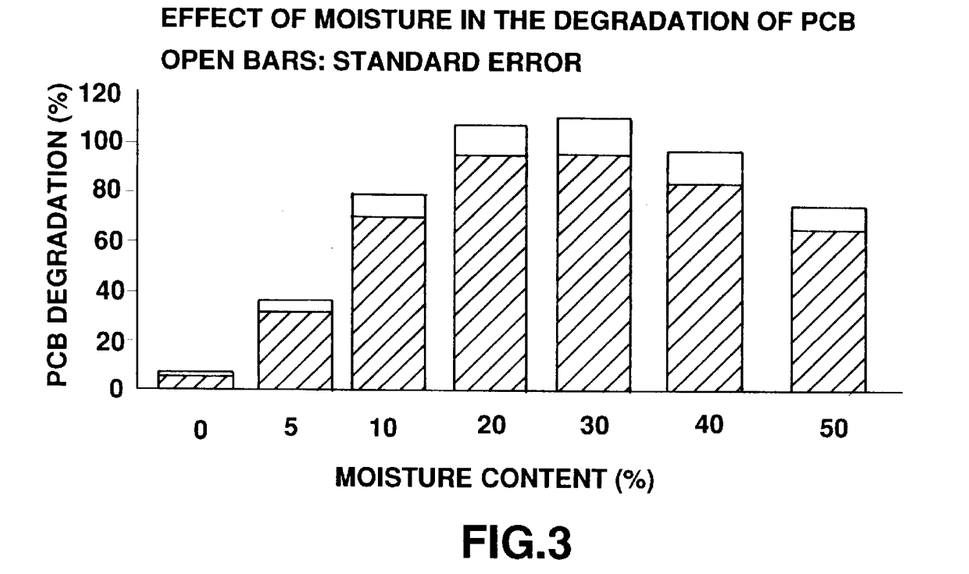
FIG. 3 shows the effect of moisture on the degradation of PCBs in accordance with the present invention.
Figure 4:
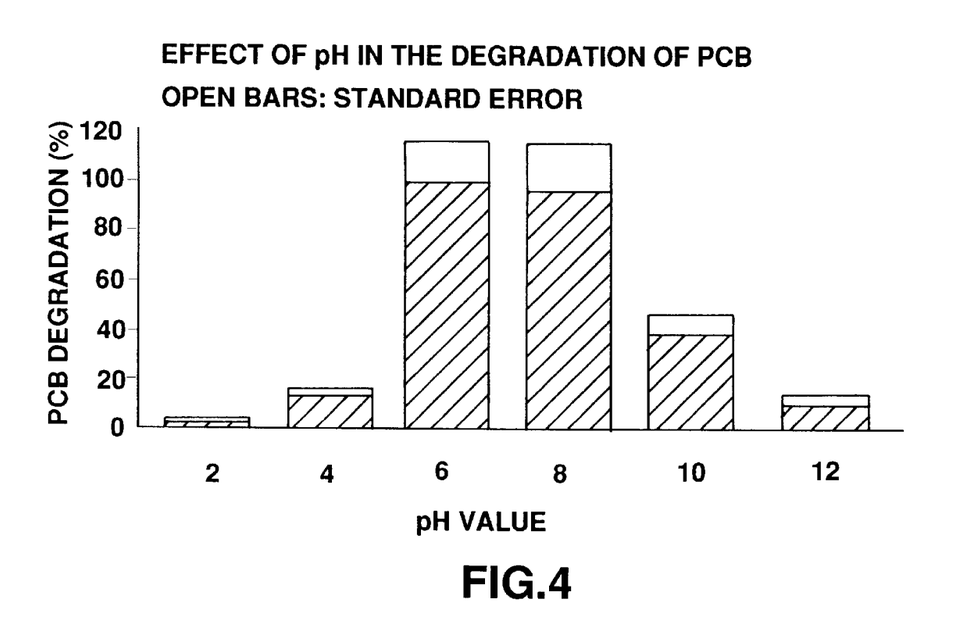
FIG. 4 shows the effect of pH on the degradation of PCBs in accordance with the present invention.

Moisture in soil is another important factor for actively growing microorganisms which in turn affects the PCBs degradation. As shown in FIG. 3, the optimal moisture content required in soil is around 20–30% whereas moisture content greater than 30% or below 10% dramatically affects the degradation of PCBs by the microorganisms.

The growth of microorganisms is also sensitive to pH. Therefore, it was important to determine the optimal pH in soil for the degradation of PCBs. It is clear from FIG. 4 that the optimal degradation of PCBs occured between pH 6–8, while extreme pH dramatically affected PCB degradation.

Figure 5:
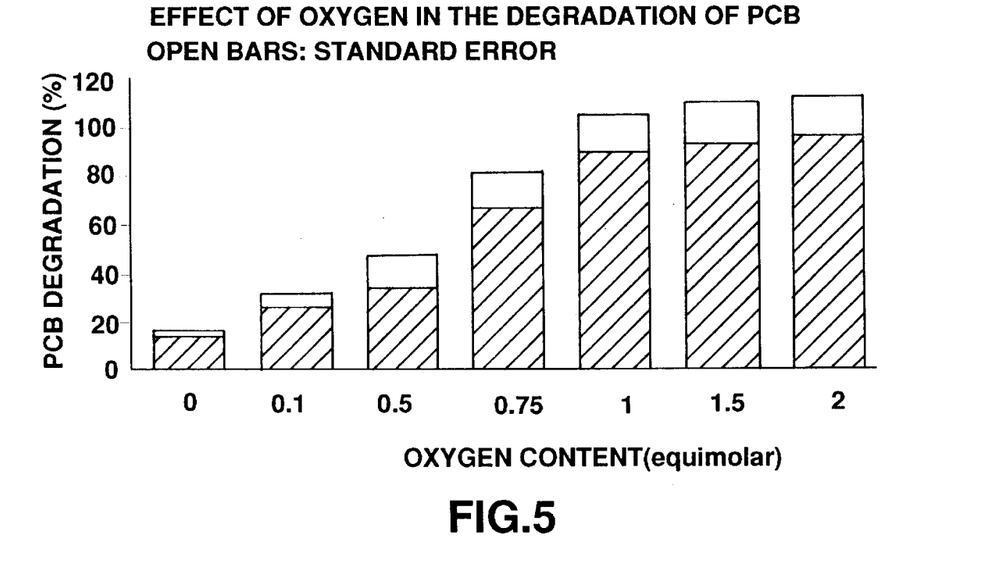
FIG. 5 shows the effect of oxygen on the degradation of PCBs in accordance with the present invention.

Another factor tested is the oxygen level in soil since it is critical for the growth of microorganisms. FIG. 5 shows that at least 1.5–2 equimolar oxygen level in soil is required for the optimal degradation of PCB whereas oxygen level lower than 1 equimolar is not sufficient.

Figure 6:
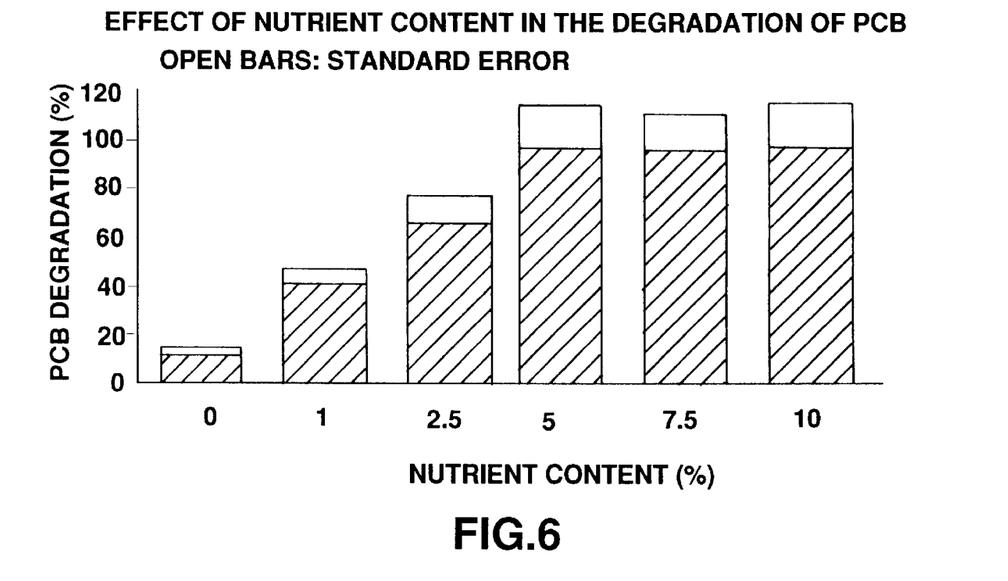
FIG. 6 shows the effect of nutrient content on the degradation of PCBs in accordance with the present invention.

Apart from the conditions described above, microorganisms have absolute nutritional requirements. The nutrients required for growth of the bacteria are carbon, nitrogen, phosphorus, iron, magnesium and other trace minerals already present in the soil. The majority of the carbon requirements are fulfilled from a variety of hydrocarbons present in soil such as PCBs. Nitrogen, phosphorus ($PO_4$), iron and magnesium were added as described above to meet the other nutrient needs of the bacteria. Soil deficient in any of the above nutrients can lead to slower rates of microorganisms growth. The minimal requirements of nutrients required for the microorganisms to function and degrade PCBs other than hydrocarbons is shown in FIG. 6. This Figure illustrates that 5–10% of the nutrients (carbon, nitrogen and phosphorus) in soil is required for the optimal degradation of PCBs by the mixture of microorganisms used. Levels beyond 10% have little effect in improving the rate of biodegradation.

Figure 7:
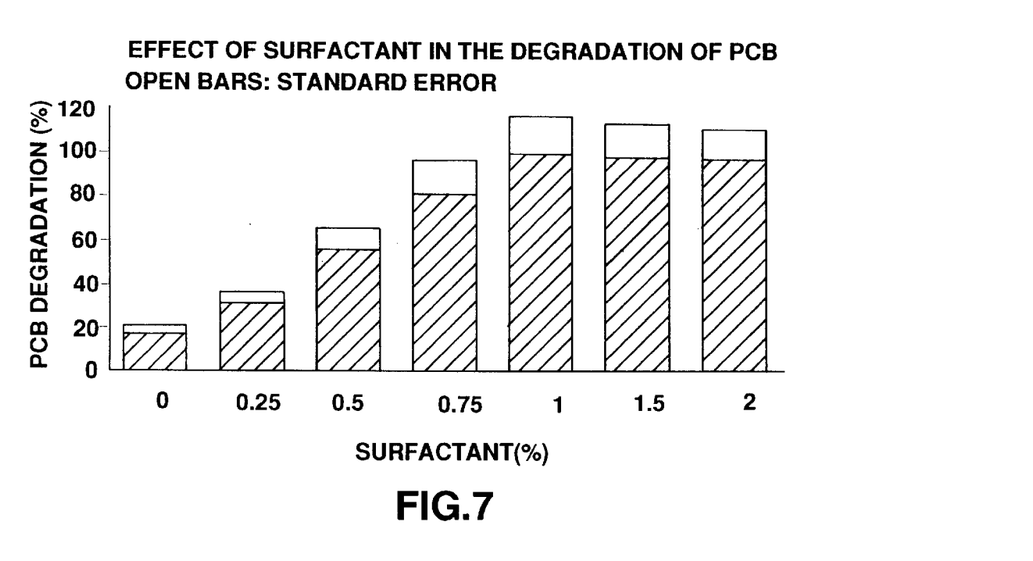
FIG. 7 shows the effect of surfactant on the degradation of PCBs in accordance with the present invention.

In soil the turnover of PCBs by the microorganisms is generally a slow process. This is mainly because PCBs are hydrophobic molecules and have the tendency to partition from the microorganisms in soil. Such partitioning usually leads to limited contact of PCBs with the microorganisms thus slower degradation. Addition of surfactant such as alkylenebenzene sulphonate, to soil overcomes such partitioning and enhances the degradation of PCBs. Various concentrations of surfactant was mixed with soil and tested for its ability to enhance the PCBs degradation. FIG. 7 shows that the addition of at least 1% surfactant is required for optimal degradation of PCBs in soil using the method of the present invention.

Figure 8:
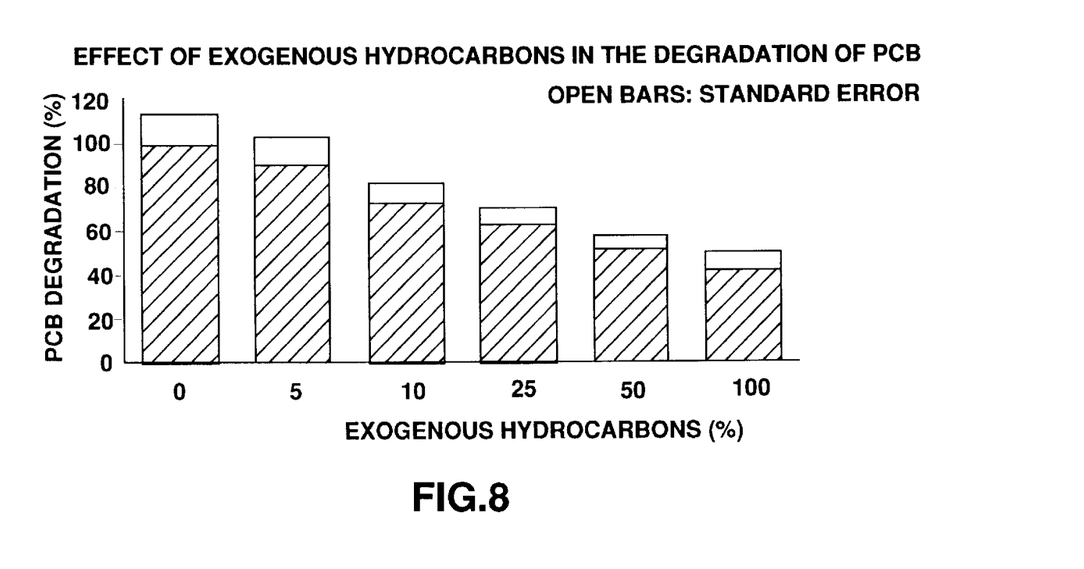
FIG. 8 shows the effect of exogenous hydrocarbons on the degradation of PCBs in accordance with the present invention.

Soil contaminated with PCBs may contain a variety of different hydrocarbons especially if it originates from a different source. If the microorganisms present in soil do not selectively degrade PCBs, then presence of hydrocarbons other than PCBs would interfere in the PCB degradation process. Therefore, it was important to determine if the microorganisms in soil are selective toward PCB degradation in soil. Addition of exogenous hydrocarbons (petroleum & non-petroleum) in soil show an inhibitory effect on the degradation of PCB and suggest that the microorganisms in soil do not selectively degrade PCBs but other hydrocarbons as well (FIG. 8).

Removal and Treatment of Contaminated Soil

Figure 9:
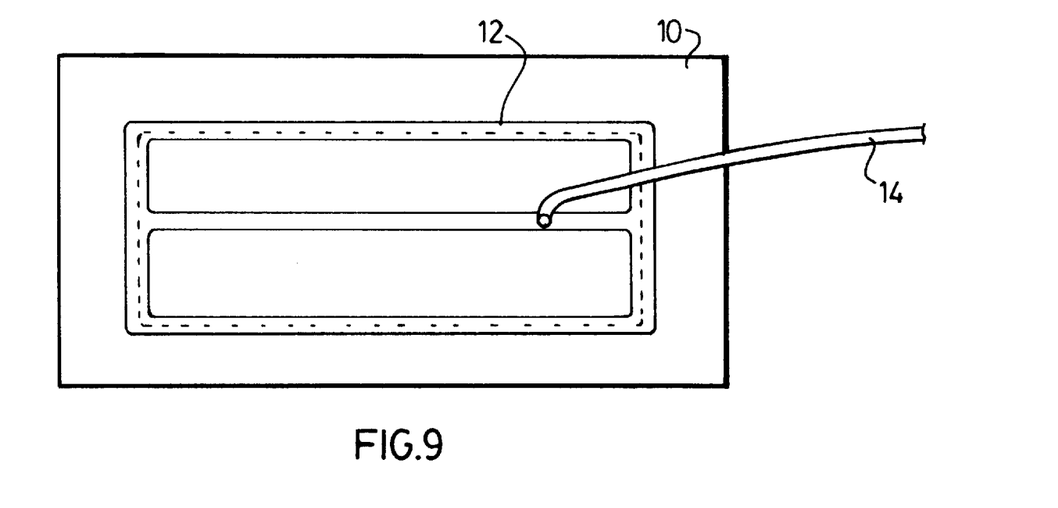
FIG. 9 is a top view of an apparatus for the degradation of PCBs in soil in accordance with the present invention.
Figure 10:
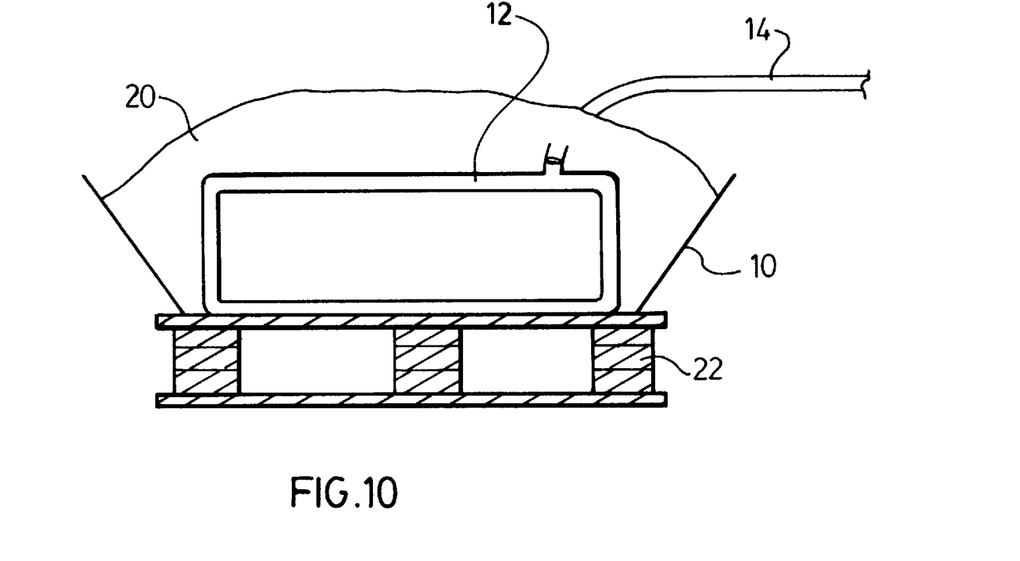
FIG. 10 is the front perspective view of an apparatus for the degradation of PCBs in soil in accordance with the present invention.

The target soil, contaminated with PCBs, was excavated from a landfill site using standard excavation techniques. It is understood by those skilled in the art that any PCB contaminated soil from any location can be used for treatment in the present method. The contaminated soil is placed in a mound, container, or apparatus and taken to a location off-site, where the conditions of the contaminated soil can be controlled. Alternatively, the soil can be treated on site. The present invention also embodies the development of mobile units comprising set of trailers which are transportable to the site of soil contamination and wherein the stringent conditions of temperature, pH, etc. can be controlled. One embodiment of such an apparatus is depicted in FIGS. 9 and 10. The apparatus should be placed inside a heated covered structure where temperature can be controlled and the apparatus is sheltered from rainfall. As seen in FIG. 9, a pipe 12, which is slotted or perforated, is contained inside a tray 10 that is made of steel or other suitable material. An air hose 14 is connected to the pipe 12.

As seen in FIG. 10, the tray 10 is placed on a platform 22. Contaminated soil 20 is loaded into tray 10. Air is pumped through air hose 14 into pipe 12, where it diffuses through the slots or perforations of pipe 12, aerating soil 20.

The conditions of the soil are then set for PCB degradation according to the following. The soil is placed in a mound, container or apparatus as described above. In the preferred embodiment, the mound, container or apparatus should be placed in a closed shelter or structure where the interior temperature of the shelter, the soil and apparatus can be controlled. Temperature, moisture, pH, oxygen, nutrient level, surfactant and concentration of microorganisms is adjusted as described below. An aliquot of at least the following six microorganisms should be obtained, preferably by the method described in the example above: Pseudomonas sp., Acinetobacter sp., *Alcaligenes eutrophus*, Polygonum sp., Digitaria sp., Bacillus sp. and Micrococcus sp.

A solution containing an appropriate concentration of the bacterial culture, nutrients, surfactant and water consisting of 1% calcium chloride, 1% ferric chloride, 1% ammonium chloride, 1% magnesium sulfate, 1% phosphate buffer, 1% surfactant and 94% water is prepared and sprayed onto the soil using industry standard spray equipment until the level of bacteria reaches $25 \times 10^8$–$25 \times 10^{10}$ CFU/Kg of soil. The number of bacteria in the soil is measured by taking samples initially and every week thereafter using the standard serial dilution method to determine the number of Colony Forming Units (CFU) in the sample.

The soil is mixed during the application of the bacterial culture solution to the soil to ensure uniform distribution of the solution, either by hand or shovel, or through the use of a commercial mixer.

In the preferred embodiment, the temperature of the soil in the shelter or apparatus is raised to 32 degrees Celsius using industry standard heating methods. The number of bacteria, moisture, pH, oxygen and nutrient levels is determined by taking samples initially and once every 7 days, measuring the bacterial level, moisture level and the levels of oxygen, nitrogen, phosphorus, iron, magnesium and pH using commercially available laboratory equipment. Additional amounts of the bacterial culture solution should be added as necessary whenever: bacterial levels fall below $25 \times 10^8$–$25 \times 10^{10}$ CFU/Kg of soil, moisture levels fall below 20% or any of the individual nutrients falls below 1%. The level of pH should be controlled by the addition of phosphate buffer so that the pH is maintained between 6–8. The level of oxygen is maintained at 1.5–2.0 equimolar and controlled by turning the soil over, either by hand and shovel, or through the use of a commercial mixer, at least once every 48 hours. The level of oxygen can be determined using standard measurement techniques. The level of PCBs in the soil is monitored by taking a sample initially, and on a weekly basis thereafter, measured using gas chromatograph and electron capture detection equipment.

The above treatment of the soil is continued until the amount of PCBs have been degraded to the desired level. When the desired level of PCBs in the soil is reached, the treatment is stopped. The soil can then be returned to the site.

The method of the present invention is an improvement over known methods which require in vitro genetically engineered bacteria specific nutrient delivery systems or simply do not reduce the level of PCBs in the soil to any appreciable degree. The present invention is ideal for large scale commercial use as it can easily be used to treat at least 10–15 tonnes and in fact several fold more of contaminated soil. It is also commercially very feasible as it reduces the cost of disposal of PCB contaminated soil from about $3000 per tonne to about $35 per tonne. The present method effectively and rapidly degrades the PCBs contained in soil into non-hazardous by products. The method can reduce the level of PCB's in the soil from 2000 ppm to approximately 30 ppm or less.

Although preferred embodiments of the invention have been described herein in detail, we do not intend to limit the scope of the invention except as expressly defined in the appended claims.

I claim:

1. A method for the microbial degradation of polychlorinated biphenyls in soil into non-hazardous by products, said method comprising;

(a) adding a culture containing at least six isolated strains of microorganisms selected from the group consisting of Pseudomonas sp., Acinetobacter sp., *Alcaligenes eutrophus,* Polygonum sp., Digitaria sp., Bacillus sp. and Micrococcus sp. which are capable of degrading polychlorinated biphenyls to polychlorinated biphenyl contaminated soil, wherein said microorganisms are not genetically engineered in vitro; and (b) mixing the soil and said microorganism culture together and maintaining said mixture under stringent conditions which promote the growth of the microorganisms and which stimulate the ability of the microorganisms to degrade the polychlorinated biphenyls.

2. A method as claimed in claim 1, wherein said PCB contaminated soil is taken from a land fill site.

3. A method as claimed in claim 1, wherein said strains of microorganisms are isolated from PCB contaminated soil.

4. A method as claimed in claim 1, wherein said mixture of soil and microorganism culture is maintained at 32 degrees celsius.

5. A method as claimed in claim 1, wherein said mixture of soil and microorganism culture is maintained at a moisture content of 10–30%.

6. A method as claimed in claim 1, wherein said mixture of soil and microorganism culture is maintained at a pH of about 6 to 8.

7. A method as claimed in claim 1, wherein said mixture of soil and microorganism culture is maintained at an oxygen level of about 1.5 to 2.0 equimolar.

8. A method as claimed in claim 7, wherein said composition of nutrients comprises calcium chloride, ferric chloride, ammonium chloride, magnesium sulfate, phosphate and water.

9. A method as claimed in claim 1, wherein a composition of nutrients is provided to stimulate the growth of said microorganisms.

10. A method as claimed in claim 1, wherein a concentration of microorganisms of approximately $25 \times 10^8$–$35 \times 10^8$ CFU is maintained per kilogram of PCB contaminated soil.

11. A method as claimed in claim 1, wherein said method additionally comprises the addition of a surfactant to the mixture of soil and microorganism culture.

12. A method as claimed in claim 11, wherein 1% by weight of surfactant is added.

13. A method as claimed in claim 12, wherein said surfactant is alkylenebenzene sulfonate.

14. A method for the microbial degradation of polychlorinated biphenyls in soil into non-hazardous by products, said method comprising;

(a) adding a culture containing at least six strains of microorganisms selected from the group consisting of Pseudomonas sp., Acinetobacter sp., *Alcaligenes eutrophus,* Polygonum sp., Digitaria sp., Bacillus sp. and Micrococcus sp. capable of degrading polychlorinated biphenyls to polychlorinated biphenyl contaminated soil; and (b) mixing the soil and microorganism culture together and maintaining said mixture under the following conditions; pH 6–8, temperature at approximately 32° C., 10–30% moisture content, 1.5–2.0 equimolar oxygen and 5–10% nutrients, said conditions promoting the growth of the microorganisms and stimulation of the ability of the microorganisms to degrade polychlorinated biphenyls in said soil.

15. A method as claimed in claim 14, wherein said microorganism culture is maintained at approximately a concentration of $25 \times 10^8$–$35 \times 10^8$ CFU per kilogram of contaminated soil.

16. A method as claimed in claim 15, wherein said method additionally comprises the addition of a surfactant.

17. A method for the microbial degradation of polychlorinated biphenyls (PCBs) in soil into non-hazardous by products, said method comprising:

(a) adding a culture containing at least six isolated strains of microorganisms selected from the group consisting of Pseudomonas sp., Acinetobacter sp., *Alcaligenes eutrophus,* Polygonum sp., Digitaria sp., Bacillus sp. and Micrococcus sp. to polychlorinated biphenyl contaminated soil, wherein said microorganisms are not genetically engineered in vitro; and (b) mixing the soil and microorganism culture together for a sufficient time period at about 32° C. to degrade said PCBs contained within said soil to a level of less than about 30 ppm while simultaneously adding nutrients to said mixture comprising calcium chloride, ferric chloride, ammonium chloride, magnesium sulfate and phosphate, adding about 1% surfactant, maintaining a moisture content of about 10–30%, a pH of about 6–8, an oxygen level of about 1.5 to 2.0 equimolar in order to maintain a concentration of microorganisms of approximately $25 \times 10^8$–$35 \times 10^8$ CFU per kilogram of PCB contaminated soil.

* * * * *

UNITED STATES PATENT AND TRADEMARK OFFICE
CERTIFICATE OF CORRECTION

PATENT NO. : 5,932,472
DATED : August 3, 1999
INVENTOR(S) : Abdullah

It is certified that error appears in the above-identified patent and that said Letters Patent is hereby corrected as shown below:

On the title page, [73] Assignee, "Twin Oaks Envirormental Ltd." should read
--Twin Oaks Environmental Ltd.--.

Signed and Sealed this

Eighteenth Day of January, 2000

Attest:

Q. TODD DICKINSON

Attesting Officer

Commissioner of Patents and Trademarks